(12) United States Patent
Shturman et al.

(10) Patent No.: US 6,852,118 B2
(45) Date of Patent: Feb. 8, 2005

(54) SELF-INDEXING COUPLING FOR ROTATIONAL ANGIOPLASTY DEVICE

(75) Inventors: Leonid Shturman, Greenwich, CT (US); Georgy Vasilevich Morov, Moscow (RU); Michail Alekseevich Ermakov, Moscow (RU)

(73) Assignee: Shturman Cardiology Systems, Inc., Minneapolis, MN (US)

( * ) Notice: Subject to any disclaimer, the term of this patent is extended or adjusted under 35 U.S.C. 154(b) by 385 days.

(21) Appl. No.: 10/084,001

(22) Filed: Oct. 19, 2001

(65) Prior Publication Data

US 2003/0078594 A1 Apr. 24, 2003

(Under 37 CFR 1.47)

(51) Int. Cl.⁷ .............................................. A61B 17/22
(52) U.S. Cl. ..................................... 606/159; 606/180
(58) Field of Search ........................ 604/19, 22; 606/1, 606/107, 127, 159, 167, 170, 171, 53, 79, 80, 191–200

(56) References Cited

U.S. PATENT DOCUMENTS

| | | | |
|---|---|---|---|
| 4,990,134 A | | 2/1991 | Auth |
| 5,314,407 A | | 5/1994 | Auth et al. |
| 5,314,438 A | | 5/1994 | Shturman .................... 606/159 |
| 5,634,933 A | * | 6/1997 | McCombs et al. .......... 606/180 |
| 5,833,246 A | * | 11/1998 | Trott .......................... 279/131 |
| 5,849,023 A | * | 12/1998 | Mericle ....................... 606/180 |
| 5,928,241 A | | 7/1999 | Menut et al. .................. 606/80 |
| 6,024,749 A | | 2/2000 | Shturman et al. ........... 606/159 |
| 6,077,282 A | | 6/2000 | Shturman et al. ........... 606/159 |
| 6,129,734 A | * | 10/2000 | Shturman et al. ........... 606/159 |
| 6,132,444 A | | 10/2000 | Shturman et al. ........... 606/159 |

FOREIGN PATENT DOCUMENTS

WO        WO 96/37153        11/1996

* cited by examiner

Primary Examiner—Glenn K. Dawson
(74) Attorney, Agent, or Firm—Perman & Green, LLP

(57) ABSTRACT

A rotational angioplasty device having a handle housing and an exchangeable drive shaft cartridge. The handle housing includes a rotatable prime mover carried by a prime mover carriage which is longitudinally movable with respect to the handle housing. The exchangeable drive shaft cartridge includes a tubular core element, a longitudinally extendible tube, a catheter and a rotatable drive shaft which, near its distal end, has an abrasive tissue removal implement. The cartridge is detachable from the handle housing, the longitudinally extendible tube is detachable from the prime mover carriage, and the drive shaft together with its tissue removal implement may be attached to and detached from the prime mover, thereby permitting the exchangeable drive shaft cartridge to be selectively attached to and detached from the handle housing. A coupling is provided which connects the longitudinally extendible tube to the prime mover carriage while indexing the relative position of the longitudinally extendible tube and the proximal portion of the drive shaft.

9 Claims, 11 Drawing Sheets

SELF-INDEXING COUPLING FOR ROTATIONAL ANGIOPLASTY DEVICE

BACKGROUND OF THE INVENTION

1. Field of the Invention

The invention relates to devices and methods for removing tissue from body passageways, such as removal of atherosclerotic plaques from arteries, utilizing a rotational angioplasty device. In particular, the invention relates to improvements in a coupling between exchangeable drive shaft cartridge and prime mover carriage of a rotational angioplasty device.

2. Brief Description of Related Developments

A variety of techniques and instruments have been developed for use in the removal or repair of tissue in arteries and similar body passageways. A frequent objective of such techniques and instruments is the removal of atherosclerotic plaques in patient's arteries. Atherosclerosis is characterized by the buildup of fatty deposits (atheromas) in the intimal layer (i.e., under the endothelium) of a patient's blood vessels. Very often over time what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Rotational angioplasty procedures are a common technique for removing such stenotic material. Such procedures are used most frequently to commence the opening of cacifield lesions in coronary arteries. Often the rotational angioplasty procedure is not used alone, but is followed by a balloon angioplasty procedure. This, in turn, may frequently be followed by placement of a stent in order to prevent acute closure of the artery which has been opened.

Studies have shown, however, that a significant percentage of patients who have undergone balloon angioplasty and had a stent placed in an artery experience in-stent restenosis (i.e., blockage of the stent) which most frequently develops over a period of time as a result of excessive growth of scar tissue within the stent. Rotational angioplasty devices were utilized in removing the excessive scar tissue from the stents and, thereby were useful in providing assistance in restoring the patency of the arteries.

It should be understood that rotational angioplasty devices and rotational angioplasty procedures are often referred to as rotational atherectomy devices and rotational atherectomy procedures. These terms may be used interchangeably herein.

One example of a rotational angioplasty device is shown in U.S. Pat. No. 4,990,134 (Auth), wherein a front or distal portion of a burr is covered with an abrasive cutting material such as diamond particles. The burr itself is mounted at the distal end of a flexible drive shaft and is rotated at high speeds (typically, e.g., in the range of about 140,000–180,000 rpm) while it is advanced across the stenosis. Once the burr has been advanced across the stenosis, the artery will have been opened to a diameter equal to or only slightly larger than the maximum outer diameter of the burr. A series of different size burrs may be utilized to open the artery to a desired diameter. U.S. Pat. No. 5,314,438 (Shturman) shows another rotational angioplasty device having a drive shaft made from helically wound wires. A section of the drive shaft has an enlarged diameter. In one embodiment at least a front or distal segment of this enlarged diameter section is covered with an abrasive material to define an abrasive segment of the drive shaft. The enlarged diameter section is hollow. This Shturman Device described in the '438 patent is capable of opening an artery only to a diameter about equal to the maximum diameter of the enlarged diameter section of the drive shaft, thereby providing results similar to the Auth Device described in the '134 patent. Due to its flexibility the Shturman Device described in the '438 patent possesses certain advantages over the Auth Device described in the '134 patent. Another example of a rotational angioplasty device is provided in U.S. Pat. No. 6,132,444 issued to Shturman which describes a rotational atherectomy device having a flexible, elongated, rotatable drive shaft with an eccentric enlarged diameter section. At least part of the eccentric enlarged diameter section has a tissue removing surface with an abrasive surface to define a tissue removing segment of the drive shaft. When placed within an artery against stenotic tissue and rotated at sufficiently high speeds (e.g. in the range of about 60,000 rpm to about 200,000 rpm) the eccentric nature of the enlarged diameter section of the drive shaft causes such section to rotate in such a fashion as to open the stenotic lesion to a diameter substantially larger than the maximum diameter of the enlarged diameter section.

U.S. Pat. No. 5,314,407 (Auth) shows details of a type of handle which may be used in conjunction with rotational atherectomy devices of the type shown in the Auth '134 and Shturman '438 and '444 patents. A handle of the type shown in the Auth '407 patent has been commercialized by Heart Technology, Inc. (Redmond, Wash.), now owned by Boston Scientific Corporation (Natick, Mass.) in the rotational atherectomy device sold under the trademark Rotablator®. The handle of the Rotablator®. device includes a variety of components, including a compressed gas driven turbine, a mechanism for clamping a guide wire extending through the drive shaft, portions of a fiber optic tachometer, and a pump for pumping saline around the drive shaft.

The connection between the drive shaft (with its associated burr) and the turbine in the Rotablator®. device is permanent; yet, frequently it is necessary to use more than one size burr during an atherectomy procedure. That is, often a smaller size burr is first used to open a stenosis to a certain diameter, and then one or more larger size burrs are used to open the stenosis further. Such use of multiple burrs of subsequently larger diameters is sometimes referred to as a "step up technique" and is recommended by the manufacturer of the Rotablator® device. In the original multiple burr technique it was necessary to use a new Rotablator® device for each such successive size burr. Accordingly, there was a need for an atherectomy system that would permit a physician to use only one handle throughout an entire procedure and to attach to such handle an appropriate drive shaft and tissue removing implement (e.g., a burr) to initiate the procedure and then exchange the drive shaft and the tissue removing implement for a drive shaft having a tissue removing implement of a different size or even a different design.

A subsequent version of the Rotablator® device has been introduced with the ability to exchange a flexible distal portion of the drive shaft together with a burr for another distal portion of a drive shaft having a different size burr. Technical details of such a system are contained in international patent application No. WO 96/37153. This system utilizes a flexible drive shaft having a connect/disconnect feature allowing the physician to disconnect the exchangeable distal portion of the flexible drive shaft, together with the burr, from the flexible proximal portion of the drive shaft which is connected to the turbine of the handle, thus permitting the burr size to be changed without discarding the entire atherectomy unit.

Each exchangeable drive shaft portion is disposed within its own exchangeable catheter and catheter housing. The flexible proximal portion of the drive shaft in this system is permanently attached to the turbine and is not exchanged. This system has been commercialized by Boston Scientific under the trademark Rotablator®, RotaLink™ System. While the Rotablator® RotaLink™ System does permit one to change the burr size, the steps required to actually disconnect the exchangeable portion of the drive shaft and replace it with another exchangeable portion of the drive shaft are quite involved and require relatively intricate manipulation of very small components.

First, a catheter housing must be disconnected from the handle and moved distally away from the handle to expose portions of both the proximal and distal sections of the flexible drive shaft which contain a disconnectable coupling. This coupling is disconnected by sliding a lock tube distally, permitting complementary lock teeth on the proximal and distal portions of the flexible drive shaft to be disengaged from each other. A similar flexible distal drive shaft portion with a different burr may then be connected to the flexible proximal portion of the drive shaft. To accomplish such assembly, the lock tooth on the proximal end of the distal replacement portion of the drive shaft must first be both longitudinally and rotationally aligned with the complementary lock tooth at the distal end of the proximal portion of the drive shaft. Since the flexible drive shaft typically is less than 1 mm in diameter, the lock teeth are similarly quite small in size, requiring not insignificant manual dexterity and visual acuity to properly align and interlock the lock teeth. Once the lock teeth have been properly interlocked with each other, the lock tube (also having a very small diameter) is slid proximally to secure the coupling. The catheter housing must then be connected to the handle housing.

While this system does permit one to exchange one size burr (together with a portion of the drive shaft) for a burr of another size, the exchange procedure is not an easy one and must be performed with considerable care. The individual performing the exchange procedure must do so while wearing surgical gloves to protect the individual from the blood of the patient and to maintain the sterility of the elements of the system. Surgical gloves diminish the tactile sensations of the individual performing the exchange procedure and therefore make such exchange procedure even more difficult.

Accordingly, it would be desirable to have an atherectomy device permitting easier attachment and/or exchange of the drive shaft and its tissue removing implement.

SUMMARY OF THE INVENTION

The invention provides a rotational atherectomy device designed to facilitate easy attachment, detachment and exchange of the drive shaft and its tissue removing implement. The rotational atherectomy device includes a handle housing and an exchangeable drive shaft cartridge which is removably attachable to the handle housing. A rotatable prime mover is carried by a prime mover carriage disposed within the handle housing, the prime mover carriage being longitudinally movable with respect to the handle housing. The exchangeable drive shaft cartridge includes a cartridge housing which is removably attachable to the handle housing, a longitudinally movable tube disposed within the cartridge housing, the tube having a proximal end portion that is removably attachable to the prime mover carriage, and a rotatable flexible drive shaft. The drive shaft has a proximal portion which is disposed within the longitudinally movable tube and a distal portion which includes a tissue removal implement. A drive shaft attachment mechanism is provided to removably attach the proximal portion of the drive shaft to the prime mover.

Because the drive shaft is mounted within the longitudinally moveable tube for free rotation therein, there is a need to provide a mechanism for permitting an axially applied attachment and detachment force to be applied to the proximal end of the drive shaft during attachment to and detachment from the prime mover, but without limiting the free rotation of the drive shaft in operation. This axial force allows the proximal end of the drive shaft to be engaged with the prime mover. There is also a need to connect the longitudinally moveable tube with the prime mover carriage to allow the axial movement of the combined assembly of the prime mover carriage and the drive shaft during rotation of the prime mover and drive shaft. This connection must position the proximal end of the drive shaft relative to the longitudinally moveable tube to enable free rotation thereof with respect to the tube.

It is the connection of prime mover carriage to the longitudinally moveable tube to which this invention is directed. In particular the connection must operate in the attached condition to index the relative position of the longitudinally moveable tube so that there is a clearance with the abutment surfaces of the proximal end of the drive shaft.

To accomplish the axial position adjustment of the proximal end of the drive shaft, a resilient annular element is inserted at the interface of moveable tube and a coupling cylinder which is integral with the prime mover carriage. The outer surface of the moveable tube and the inner surface of the coupling cylinder are constructed with strategically positioned annular grooves. One of the grooves, referred to as the retention groove, provides a seat for retention of the resilient annular element to hold the resilient element in place on one of the interface surfaces while the other interface surface is allowed to move axially subject to the radial force of the resilient element.

The other annular groove, referred to as the index groove, is constructed in the form of a shallow groove the surfaces of which act as cam surfaces to allow the movement and expansion of the resilient element into the groove. The relative position of the retention and index grooves is important to provide the needed indexing of the drive shaft position with respect to the moveable tube to provide the necessary clearance.

BRIEF DESCRIPTION OF THE DRAWINGS

FIG. 5b is an enlargement of FIG. 5a;

DETAILED DESCRIPTION OF THE PREFERRED EMBODIMENT(S)

Figure 1:
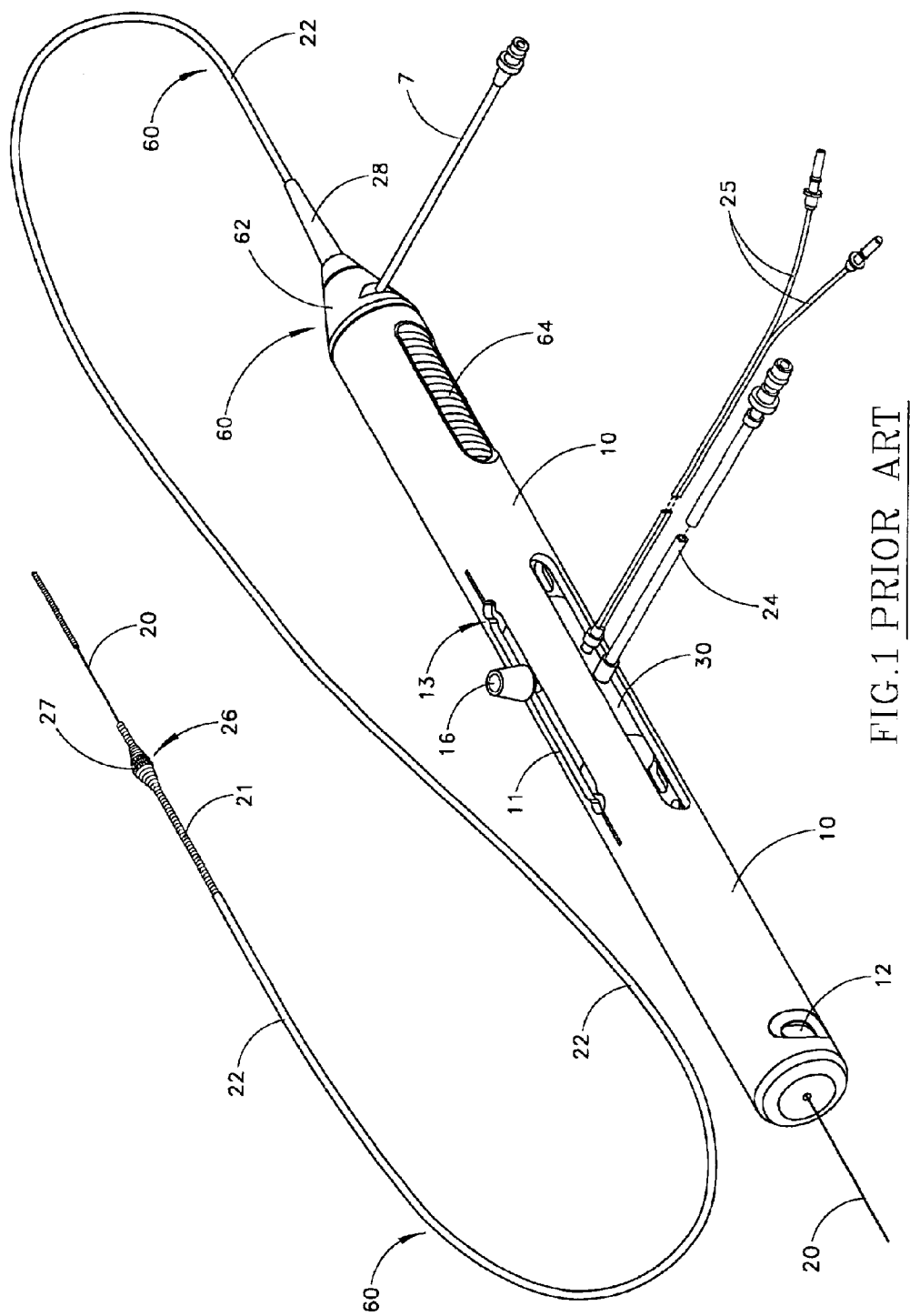
FIG. 1 is a perspective view of a rotational atherectomy device of the prior art.

FIG. 1 illustrates a rotational atherectomy device having an exchangeable drive shaft cartridge. The device desirably includes a tubular handle housing 10. The handle housing 10 has a proximal portion which carries a guide wire clamp or brake mechanism 12, an intermediate portion which carries a prime mover carriage 30, and a distal portion which is adapted to releasably interlock with an exchangeable drive shaft cartridge 60. The details of this system are described in U.S. Pat. Nos. 6,024,749 and 6,077,282 both of which issued to Shturman, the disclosures of which are incorporated herein in their entirety by reference.

The prime mover carriage 30 can be moved longitudinally within the handle housing 10 through a limited range of motion. A control knob 16 (operatively secured to the prime mover carriage 30) is provided to facilitate advancing and retracting the prime mover carriage 30 with respect to the handle housing 10. This allows the distal end of the drive shaft to be moved within its range of operating positions.

Figure 2:
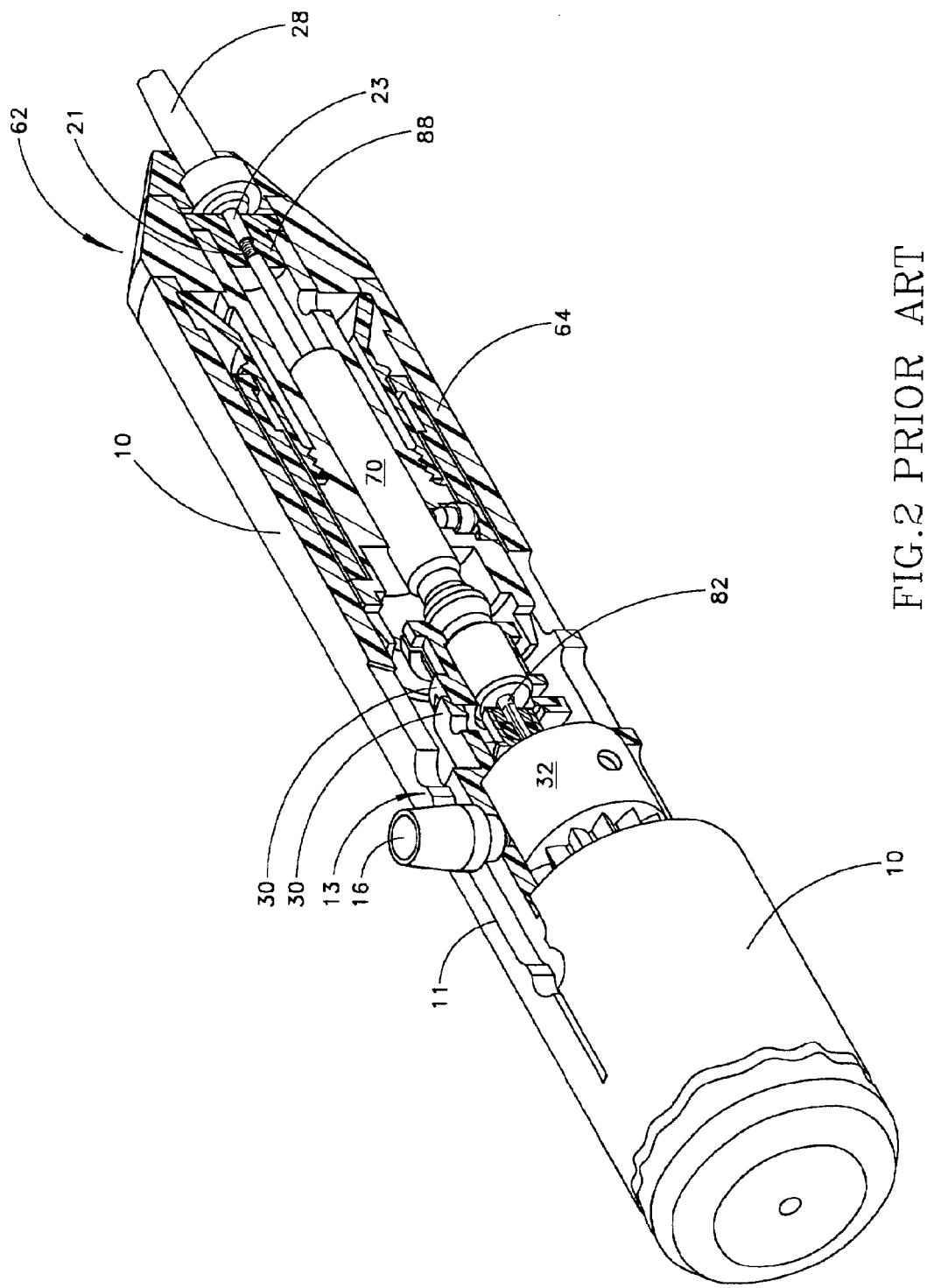
FIG. 2 is an enlarged perspective, partially broken-away view of a portion of the device shown in FIG. 1, illustrating an exchangeable drive shaft cartridge connected to the handle housing, according to the prior art.
Figure 3:
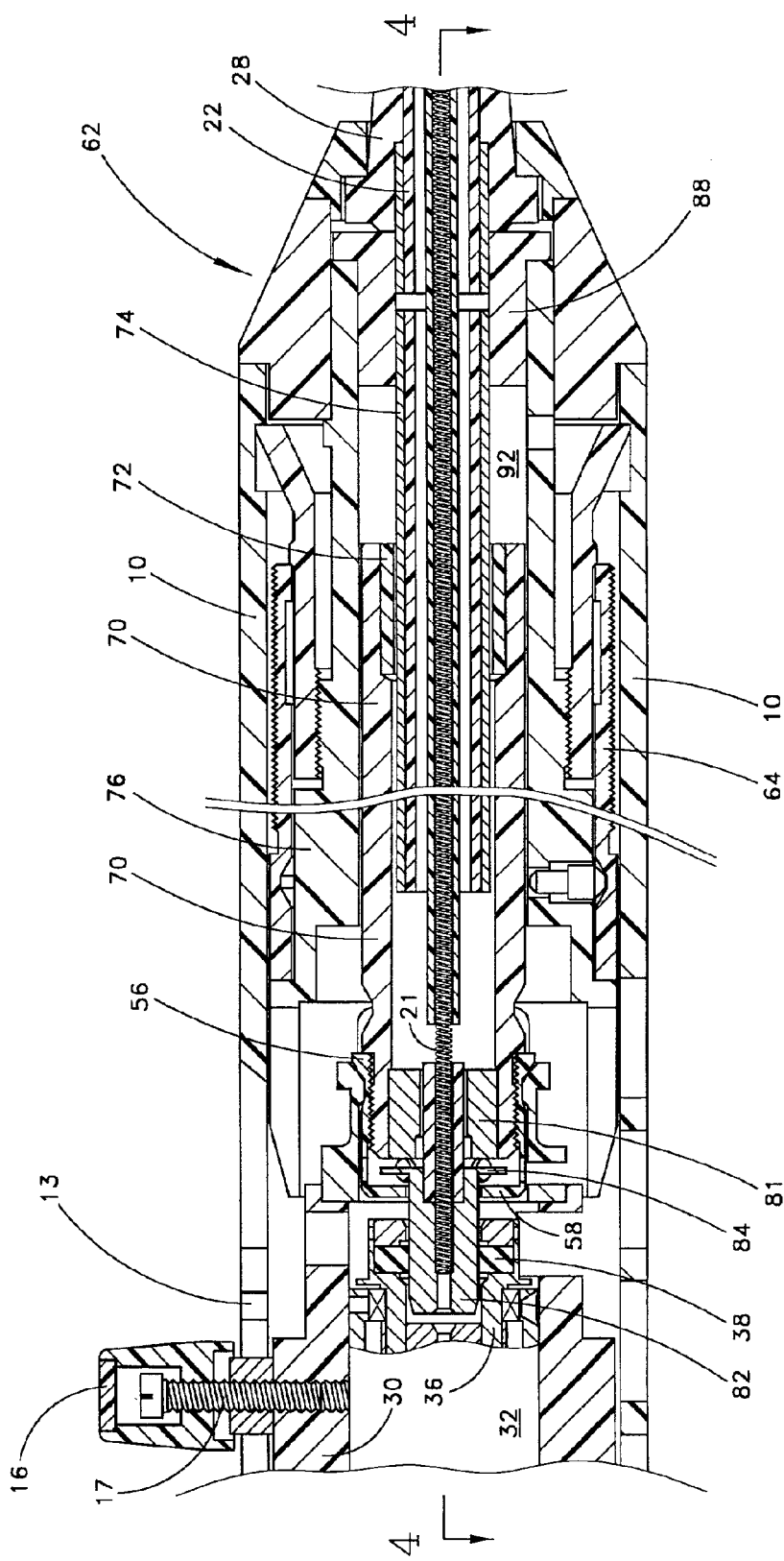
FIG. 3 is a broken away, longitudinal cross-section of the atherectomy device shown in FIG. 2.
Figure 4:
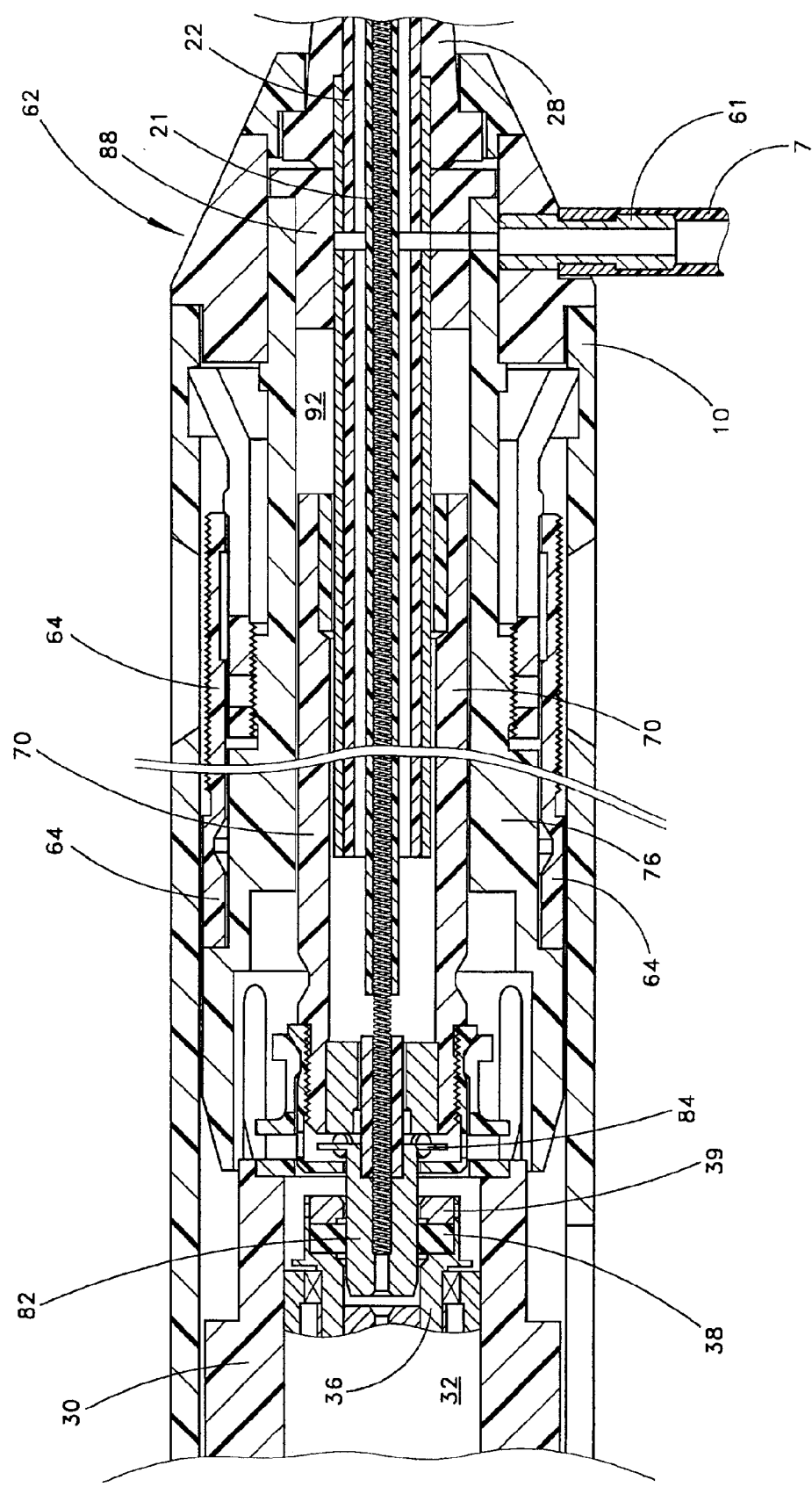
FIG. 4 is a longitudinal cross-sectional view of FIG. 3, taken along lines 4—4 thereof, and illustrating a flexible fluid supply tube attached to the exchangeable drive shaft cartridge.

The prime mover carriage 30 carries a prime mover 32. The prime mover 32 is shown in FIGS. 2–4. Preferably the prime mover is a compressed gas driven turbine. The turbine may be powered by, e.g., compressed nitrogen or compressed air. For this purpose a compressed gas supply line 24 may be provided, the supply line 24 being connected to the prime mover carriage 30. A pair of fiber optic cables 25 may also be provided for monitoring the speed of rotation of the turbine (e.g., as described in the Auth '407 patent and implemented in the Rotablator® device).

The exchangeable drive shaft cartridge 60 includes a cartridge housing 62, an elongated catheter 22 extending distally from the cartridge housing 62, a rotatable flexible drive shaft 21 disposed within the catheter 22, a longitudinally movable slide 64, and a longitudinally movable tube 70 carried within the cartridge housing 62. The longitudinally movable tube 70, as well as other components are discussed below in connection with FIGS. 2–4. The elongated catheter 22 is carried by the cartridge housing 62 and has a proximal end portion which is disposed within a short rigid tube 23. The rigid tube 23 is secured within a generally tubular end piece 88 of the cartridge housing 62. Preferably a strain relief element 28 is disposed around the distal portion of the rigid tube 23 and the proximal portion of the catheter 22. The strain relief element 28 also is secured to the cartridge housing 62.

The exchangeable drive shaft cartridge 60 includes a flexible fluid supply tube 7. One end of the fluid supply tube 7 communicates with an external fluid supply (not shown) while the other end of the tube 7 is attached to a rigid fitting 61 of the cartridge housing 62. The flexible fluid supply tube 7 is in fluid communication with the inner lumen of the catheter 22 (see, e.g., FIG. 4), supplying fluid to help reduce friction between the rotating drive shaft 21 and non-rotating elements disposed within (i.e., the guide wire 20) and around the drive shaft 21.

The flexible drive shaft 21 is rotatable over a guide wire 20 and includes a proximal portion, an intermediate portion, and a distal portion. The proximal portion of the drive shaft 21 is removably attachable to the prime mover. This portion of the drive shaft is not visible in FIG. 1. The intermediate portion of the drive shaft 21 is disposed primarily within the catheter 22 and therefore also is not visible in FIG. 1. The distal portion of the drive shaft 21 extends distally from the catheter 22 and includes a tissue removal implement 26. The tissue removal implement 26 in the illustrated embodiment comprises an eccentric enlarged diameter section of the drive shaft 21. A portion of the eccentric enlarged diameter section is covered with an abrasive material to define an abrasive segment 27 of the drive shaft 21. The diamond-coated burr attached at the distal end of the drive shaft and described by Auth in U.S. Pat. No. 4,990,134 may also be used. It should be understood that any suitable tissue removal implement may be used.

By comparing FIG. 1 with FIG. 2 one can see that the structure in FIG. 2 is not quite to scale with respect to FIG. 1. For example, the slot 11 is considerably shortened in FIG. 2 with respect to FIG. 1. In many other drawings (particularly longitudinal cross-sections) the diameter of the device and its components, as well as wall thickness, have been exaggerated so that the structural details of the device can be more clearly depicted and understood. The atherectomy device depicted in FIG. 1 is generally to scale, except for the length of the catheter 22 and drive shaft 21, which are actually substantially longer. Deviations from scale in the drawings should be readily apparent to one of ordinary skill in the art.

A drive shaft attachment mechanism is provided to removably attach the drive shaft 21 to the prime mover. The drive shaft attachment mechanism comprises a prime mover socket 38 carried by the hollow prime mover 36, and an elongated shank 82 carried by the proximal end portion of the drive shaft 21. The drive shaft shank 82 is removably insertable into the prime mover socket 38. Preferably at least one of the drive shaft shank 82 and the prime mover socket 38 is radially resilient. In the preferred embodiment shown in the drawings, the prime mover socket 38 is resilient. The prime mover socket 38 may be made to be radially resilient in a variety of ways. In the drawings the prime mover socket 38 consists of a resilient collar secured inside a recess in the hollow turbine shaft 36 by a cap 39. A variety of other suitable ways may also be utilized to secure a prime mover socket 38 to the turbine shaft 36.

The inner diameter of the prime mover socket 38 is selected to provide a sufficiently tight interference fit with the drive shaft shank 82 so that, when the drive shaft 21 is attached to the prime mover, the shank 82 and the drive shaft 21 will both rotate and move longitudinally together with the prime mover socket 38 and the prime mover when the prime mover is rotated or moved longitudinally with respect to the handle housing 10.

The elongated shank 82 is secured, either directly or indirectly, to the proximal end portion of the flexible drive shaft 21. Suitable adhesives or other conventional attachment methods may be utilized to attach the shank 82 to the flexible drive shaft 21. Moreover, the proximal end portion of the drive shaft 21 can itself constitute the shank if it is constructed in such a fashion as to be removably insertable into the prime mover socket 38.

The elongated shank 82 preferably includes proximal and distal portions. A substantial length of the proximal portion is removably insertable into the prime mover socket 38, while the distal portion preferably includes a radially outwardly extending flange 84. As shown in FIGS. 3–4, the flange 84 is positioned between (and spaced away from) proximal and distal abutment surfaces associated with the proximal end portion of the longitudinally movable tube 70. The flange 84 abuts the distal abutment surface associated with the longitudinally movable tube 70 when the shank 82 is inserted into the prime mover socket 38. The flange 84 abuts the proximal abutment surface associated with the longitudinally movable tube 70 when the shank 82 is pulled out of the prime mover socket 38. The distal abutment surface associated with the tube 70 in this embodiment is formed by bushing 81 and/or the tube 70 itself. The proximal abutment surface associated with the tube 70 is formed by a flange 58 of the collar 56 carried by (and forming a distal end of) the longitudinally movable tube 70.

The longitudinally movable tube 70 is carried within the tubular core 76 of the cartridge housing 62 and has a proximal end portion which is removably attachable to the prime mover carriage 30 for longitudinal movement therewith. The longitudinally movable tube 70 surrounds a length of the flexible drive shaft 21 and facilitates longitudinal movement of the drive shaft 21 (together with the prime mover) with respect to the handle housing 10, the cartridge housing 62 and the catheter 22.

The longitudinally movable tube 70 is slidably received in an elongated annular space 92 defined within the tubular core 76 of the cartridge housing 62. The movable tube 70 is longitudinally moveable within that annular space 92 with respect to the cartridge housing 62. Desirably at least a portion of the inner surface of the longitudinally movable tube 70 is provided with a low-friction lining 72. The lining 72 helps minimize friction between the movable tube 70 and the stationary tube 74 as the longitudinally movable tube 70 is moved proximally and distally. The lining 72 may be made from any suitable material, such as polytetrafluoroethylene tubing. If so desired, the lining may be omitted and the movable tube 70 itself may be made of a low friction material.

The atherectomy device also includes a tube attachment mechanism positioned to removably attach the longitudinally movable tube 70 to the prime mover carriage 30. The tube attachment mechanism, as shown in FIGS. 2–4, includes a resilient positioning mechanism for moving the prime mover carriage 30 and the shank 82 proximally with respect to the longitudinally movable tube 70 after the longitudinally movable tube 70 has been attached to the prime mover carriage 30 and after the prime mover carriage 30 has been moved to its range of working positions (i.e., the control knob 16 and its shaft 17 have been moved proximally through the narrowed segment 13). The resilient positioning mechanism spaces the flange 84 of the shank 82 away from both distal and proximal abutment surfaces associated with the longitudinally movable tube 70 to permit free rotation of the shank 82 with respect to the longitudinally movable tube 70.

Examples of such attachment mechanisms are shown in U.S. Pat. Nos. 6,077,282 and 6,024,749 (issued to Shturman and cited above).

The Indexing Coupling

Figure 9:
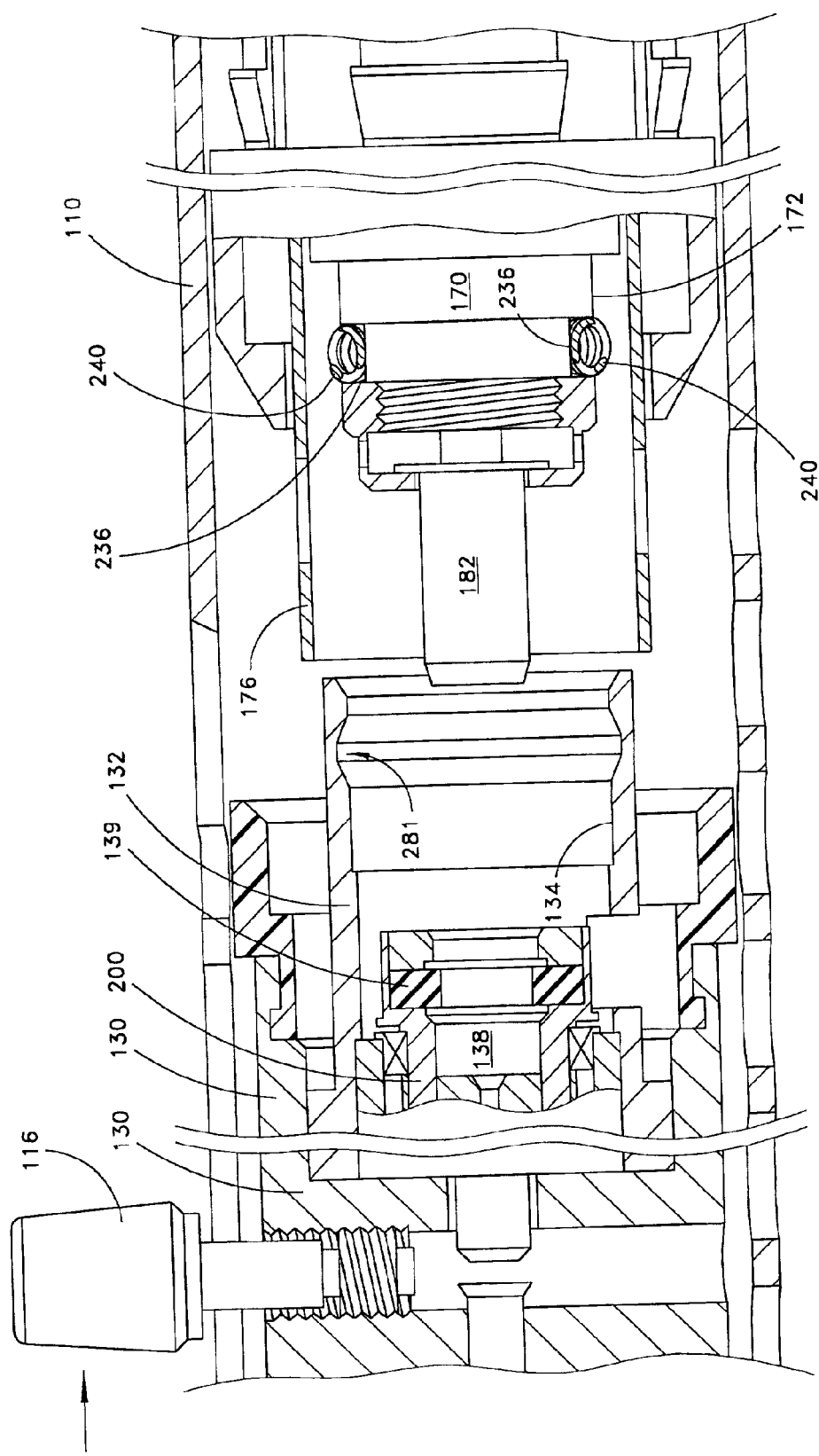
FIG. 9 is a longitudinal cross-sectional view of an alternate embodiment of this invention showing the retention groove and alignment groove reversed.
Figure 10:
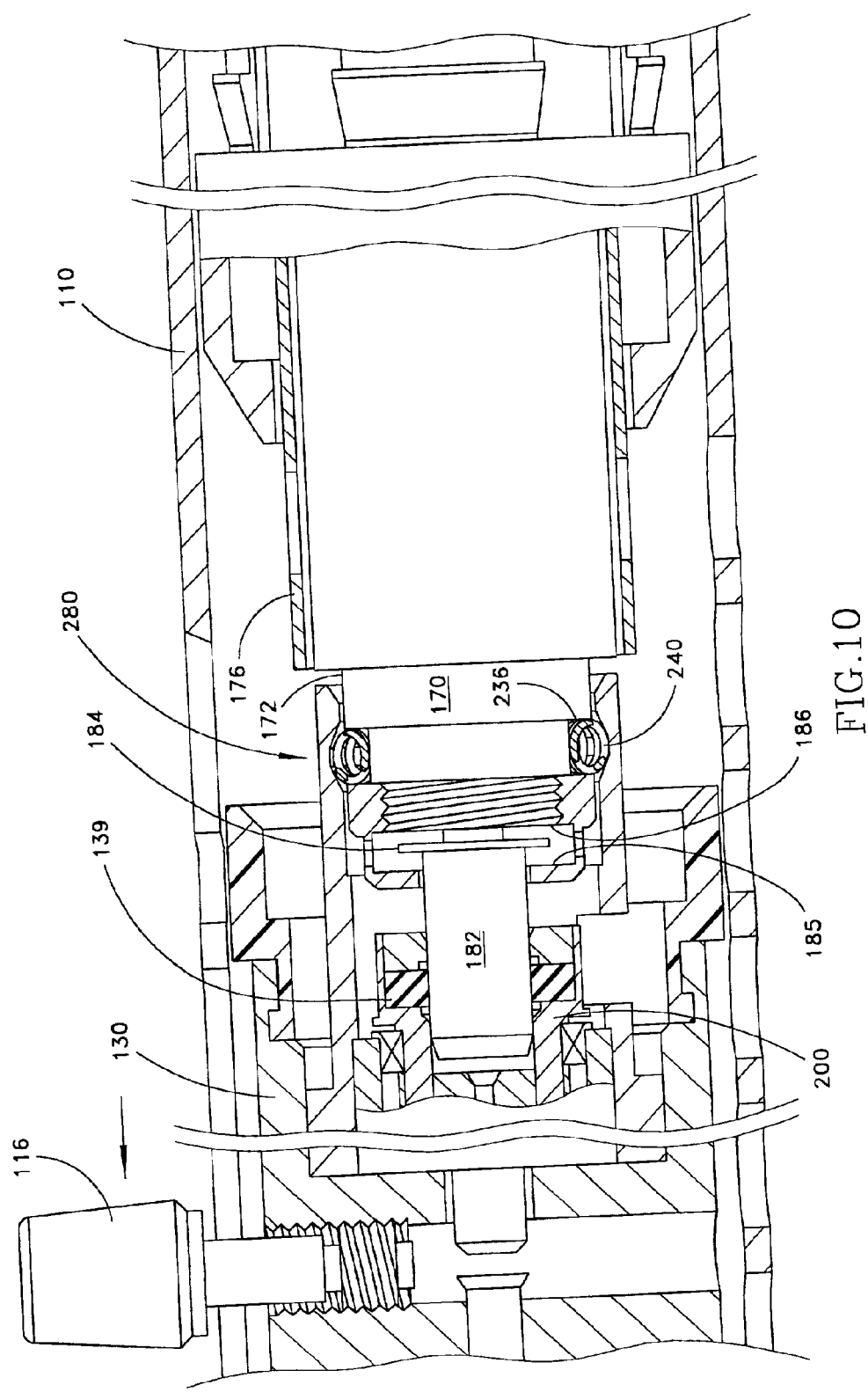
FIG. 10 is a view similar to FIG. 9 with the coupling between the prime mover carriage and the moveable tube fully engaged and the proximal portion of the drive shaft indexed for operation.

The self-indexing coupling 180 of this invention is described with reference to FIGS. 5A–10. It should be noted that only FIGS. 8 and 10 show the couplings fully assembled and the shank of the drive shaft indexed for operation. The atherectomy device, in which this invention is used, is substantially similar in operation and construction to that previously described and includes a handle housing 110. An exchangable drive shaft cartridge 162 is inserted and locked within the handle housing 110 and consists of multiple telescoping tubes as further described below.

A tubular core 176 is mounted within the cartridge 160 and provides its inner support structure. A moveable tube 170 is mounted within the tubular core 176 for axially sliding motion relative to the tubular core 176. The moveable tube 170 supports the drive shaft 121 for rotation therein.

Figure 5A:
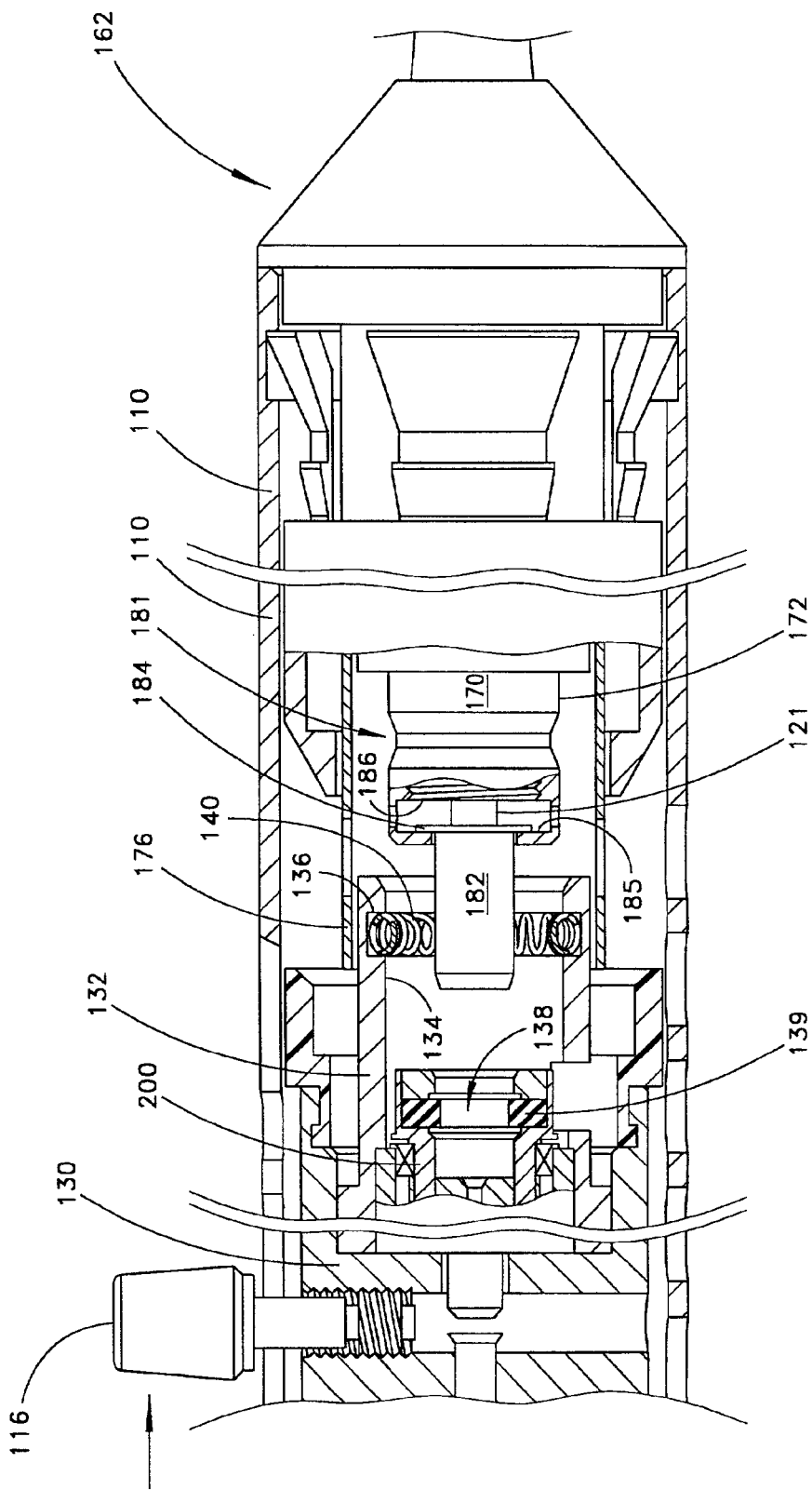
FIG. 5a is a longitudinal cross-sectional view of the connection system of this invention with the coupling between the prime mover carriage and the moveable tube disengaged.
Figure 5B:
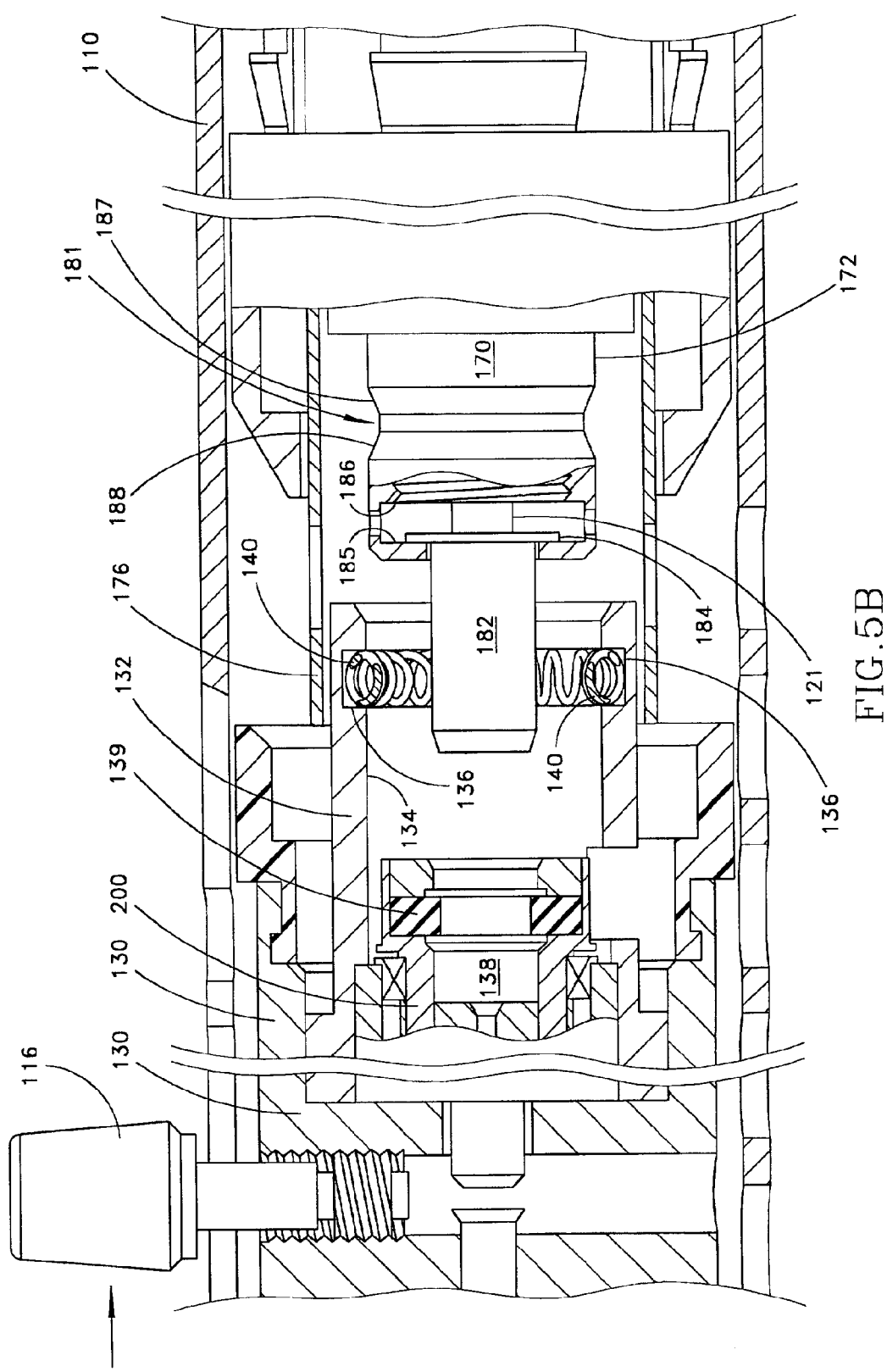

A prime mover carriage 130 is mounted within the handle housing 110 also for axial sliding motion therein in forward and reverse directions (left to right, right to left respectively in FIGS. 5a and 5b). Motion of the prime mover carriage 130 is manually actuated through lever 116. The forward end portion of the prime mover carriage 130 forms one surface of the coupling 180 of this invention and is constructed with a cylindrical coupling cylinder 132 having an inner interface surface 134.

The proximal (attachable) end of the moveable tube 170 is constructed with abutment surfaces 185 and 186, as best shown in FIGS. 5B–8. The outer surface 172 of the proximal end of tube 170 forms the other mating surface of the coupling 180 and is constructed with an annular groove 181 of reduced diameter. The groove 181 is defined by a pair of annular cam surfaces 187 and 188 best shown in FIGS. 5B–8

The purpose of the attachment coupling of this invention is to index the position of the drive shaft within its moveable tube 170 when the drive shaft 121 is operably connected to the prime mover. As best shown in FIG. 5b; The shank 182 of drive shaft 121 is inserted into the prime mover socket 138 in a friction fit provided by resilient gasket 139. As previously described shank 182 must engage moveable tube 170 during installation or removal of the drive shaft cartridge 162, but must be free to rotate at high speed, when the drive shaft cartridge is fully attached. A flange 184 extends radially outward from the distal end of shank 182 to form an abutment surface for engagement with the abutment surfaces 185 and 186 on the end of moveable tube 170. After full insertion of the shank 182 into the prime mover socket 138, there is a need to adjust the position of the shank 182 to insure the disengagement of the flange 184 from either of the abutment surfaces 185 and 186 of the moveable tube 170.

To accomplish the axial position adjustment (indexing) of the shank 182, a resilient annular element 140 is inserted at the interface of moveable tube 170 and the coupling element 132 of prime mover carriage 130. As shown in FIGS. 5a and 5b, the outer surface 172 of moveable tube 170 and the inner surface 134 of coupling element 132 are constructed with strategically positioned grooves, namely an index groove 181 and an retention groove 136 respectively.

The annular retention groove 136 provides a seat for retention of resilient annular element 140. The retention groove 136 is shaped with a rectangular cross section to hold the element 140 in place when subjected to axial forces.

Annular element 140 is formed of a shape or material which will provide a radial force between the two coupling surfaces 172 and 134. Although this force may be applied by a variety of devices, such as a resilient O-ring, it has been found that a canted coil spring formed in a ring may be advantageously used as the annular resilient element 140. Canted coil springs of this type are available from Bal Seal Engineering Company, Inc. of Santa Ana Calif. The coil spring will exert a radial force on the moveable tube 170 when engaged with surface 172.

The index groove 181 is constructed on surface 172 in the form of a shallow section of reduced cross section, formed between opposing cam surfaces 187 and 188, to permit the easy engagement of the element 140. Cam surfaces 187 and 188 are inclined in opposite directions at obtuse angles to the longitudinal axis of the moveable tube 170. The relative position of the grooves 181 and 136 is important to provide the needed indexing of the shank 182 with respect to the moveable tube 170 for the purpose of providing a clearance between the flange 184 and the abutment surfaces 185 and 186. It should be clear that the location of the grooves 181 and 136 can be reversed without departing from the scope of this invention, i.e., the retention groove 236 of the coupling 280 can be constructed in the surface 172 and the index groove 281 can be constructed in the surface 134, as shown in FIGS. 9 and 10 of the alternative embodiment of the invention. The annular canted coil spring 240 shown in FIGS. 9 and 10 may differ in size from the canted coil spring shown in FIGS. 5A–8.

Figure 6:
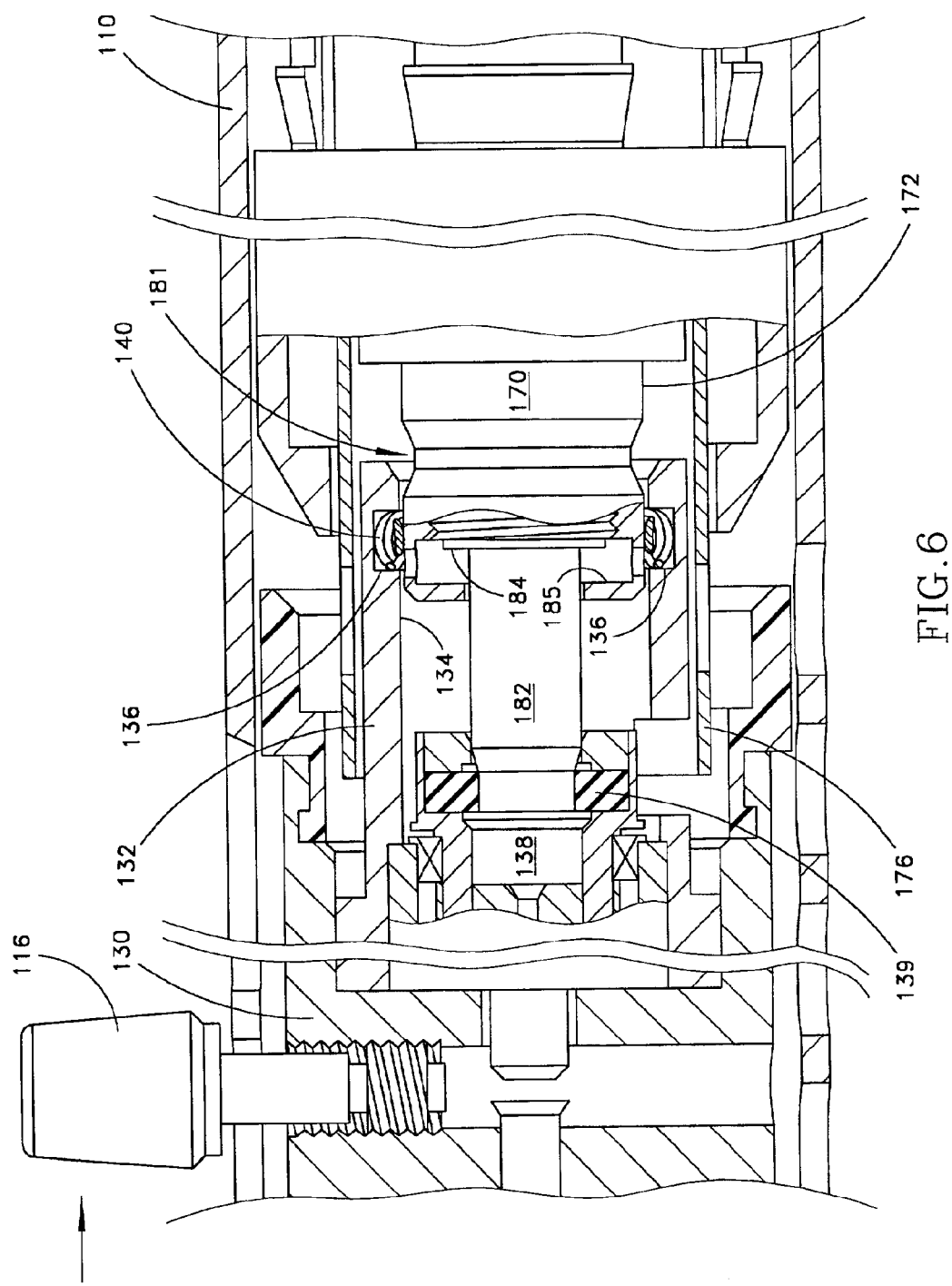
FIG. 6 is a longitudinal cross-sectional view of the connection system of this invention with the coupling between the prime mover carriage and the moveable tube partially engaged.
Figure 7:
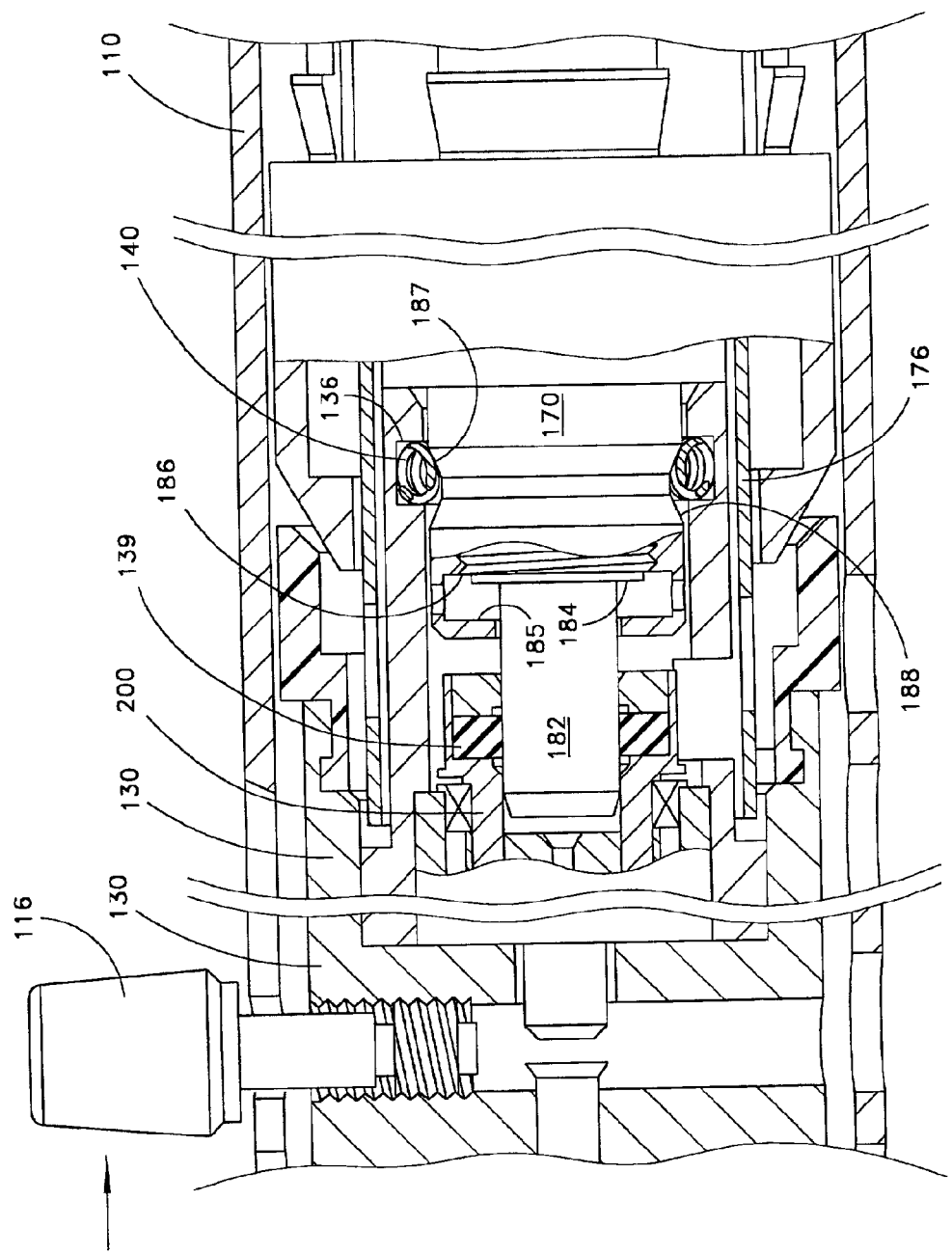
FIG. 7 is a longitudinal cross-sectional view showing the shank of the drive shaft fully inserted in the socket of the prime mover, but not yet indexed for operation by the connection system of this invention.
Figure 8:
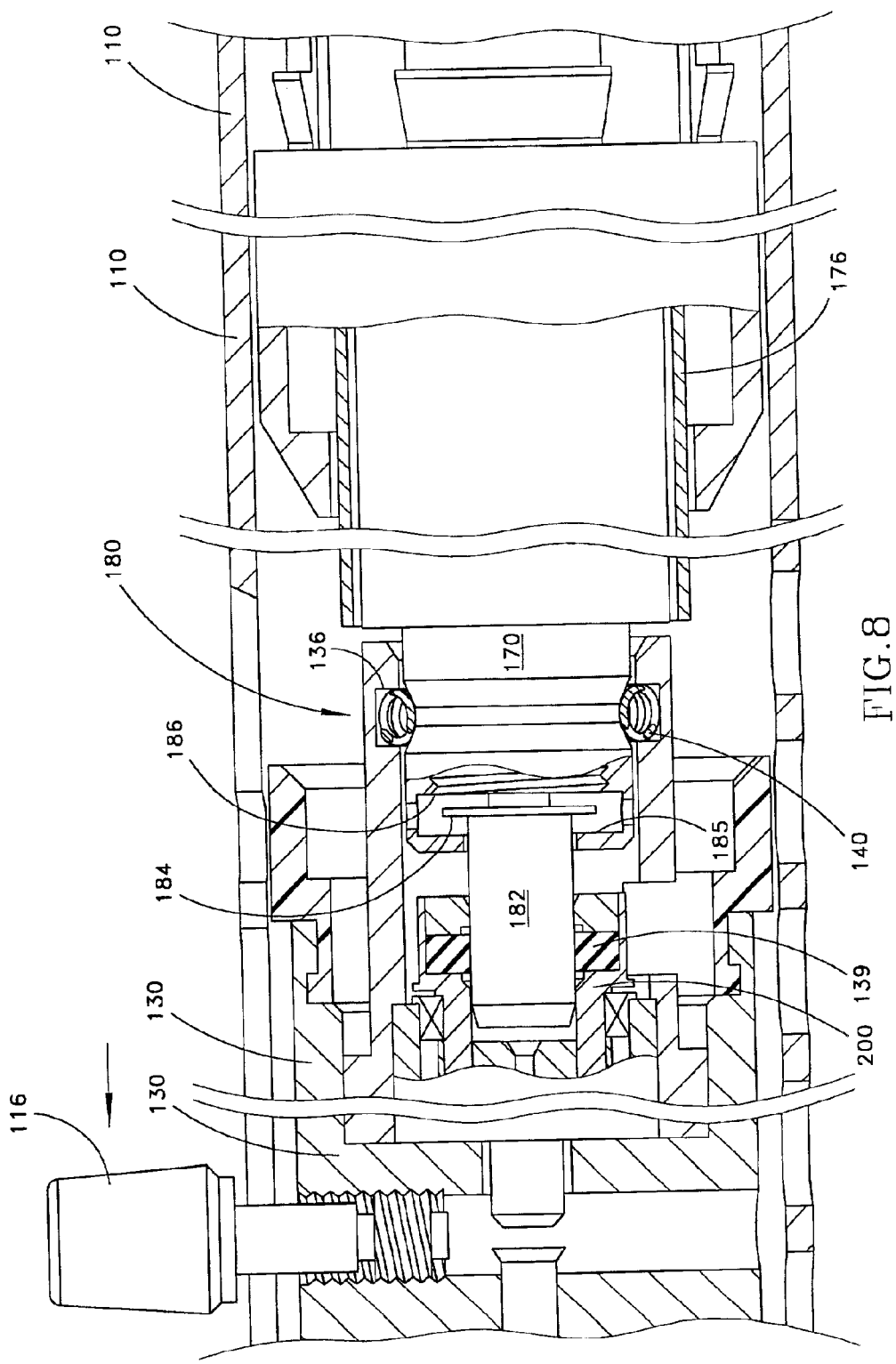
FIG. 8 is a longitudinal cross-sectional view of the connection system of this invention with the coupling between the prime mover carriage and the moveable tube fully engaged and the proximal portion of the drive shaft indexed for operation.

The operation of the coupling 180 can best be observed by reference to the relative positions of the elements as attachment progresses from FIG. 5a to FIG. 8. In FIGS. 5a and 5b shank 182 of drive shaft 121 is not yet engaged with the socket 138 of the prime mover and resilient element 140 is expanded radially in a relaxed state. With further advancement of the elements, as shown in FIG. 6, shank 182 engages the resilient member 139 within the socket 138 of the prime mover shaft 200 and resilient element 140 is compressed within retention groove 136 by engagement with surface 172. In this sequence prime mover carriage 130 is being advanced towards moveable tube 170 left to right in FIGS. 5a–6 causing the radial flange 184 of the shank 182 to abut surface 186. With further advancement as shown in FIG. 7, full insertion of the shank 182 is obtained within socket 138 to provide a driving connection between the prime mover and drive shaft 121. Resilient element 140 has engaged the indexing groove 181 and is compressed against cam surface 187. Because of the inclination of the cam surface 187, the radial force of the resilient element 140 will have a component in the axial direction, which tends to move the prime mover carriage back (to the left in FIG. 8). The axial force of the resilient member 140 may be sufficient to move the components into alignment in most instances, as soon as the user releases lever 116. However, normal operation of the lever 116 by the user may include a slight backward motion which will aid the aligning motion. As the resilient member 140 expands to more fully engage the index groove 181, the flange 184 of shank 182 moves away from abutment surface 186 to provide the clearance necessary for free rotation of the drive shaft 121 within the moveable tube 170.

In this manner a simple and easily manufactured coupling is provided which connects the moveable tube 170 to the prime mover carriage, while indexing the position of the shank 182 with respect to the moveable tube 170.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A rotational angioplasty device comprising:

a handle housing;

a rotatable prime mover carried by a prime mover carriage which is disposed within the handle housing, the prime mover carriage being longitudinally movable with respect to the handle housing;

an exchangeable drive shaft cartridge removably attachable to the handle housing further comprising:

a tubular core element mounted within the cartridge;

a longitudinally movable tube disposed within the tubular element and having a proximal end portion which is removably attachable to the prime mover carriage for longitudinal movement therewith;

a rotatable flexible drive shaft having a proximal portion which is disposed within the longitudinally movable tube and a distal portion which includes a tissue removal implement, said proximal portion having a shank at its proximal end;

a drive shaft attachment mechanism removably attaching the shank of the drive shaft to the prime mover; and a coupling for connecting said moveable tube with said prime mover carriage and adjusting the relative position of said moveable tube and said proximal portion of said drive shaft, said coupling further comprising:

a prime mover carriage coupling element fixed to said prime mover carriage having a first surface forming one part of a coupling interface;

a second surface forming a second part of said coupling interface constructed on said moveable tube, said first and second coupling surfaces overlapping in a telescoping manner to form the coupling interface;

a retention groove constructed in one of said first and second coupling surfaces in said interface;

an index groove constructed in one of said first and second coupling surfaces in said interface;

an annular resilient element positioned in said retention groove and exerting a radial force between said first and second coupling surfaces; said resilient element expanding into said index groove when said retention and index grooves are aligned;

wherein, in said aligned relation, the moveable tube and said proximal portion of said drive shaft are relatively positioned to allow rotation of said drive shaft within said moveable tube.

2. A rotational angioplasty device, as described in claim 1, wherein said shank is constructed with a radial extending flange to engage abutment surfaces on said moveable tube during axial movement of said tube and wherein, in said aligned position of said retention groove and said index groove, said flange is disengaged from said abutment surfaces.

3. A rotational angioplasty device, as described in claim 1, wherein said retention groove is constructed in said first coupling surface and said index groove is constructed in said second coupling surface.

4. A rotational angioplasty device, as described in claim 1, wherein said retention groove is constructed in said second coupling surface and said index groove is constructed in said first coupling surface.

5. A rotational angioplasty device, as described in claim 1, wherein said retention groove is constructed having rectangular cross section.

6. A rotational angioplasty device, as described in claim 1, wherein said index groove comprises an area of reduced diameter from said coupling surface defined by a first cam surface inclined from said area in a first axial direction and a second cam surface inclined from said area in a second axial direction, said second axial direction being 180° from said first axial direction.

7. A rotational angioplasty device, as described in claim 6, wherein said annular resilient element tends to be centered in said area of reduced diameter by the action of a radial spring force on said first and second cam surfaces.

8. A rotational angioplasty device, as described in claim 1, wherein said annular resilient element comprises a canted coil spring.

9. A rotational angioplasty device, as described in claim 1, wherein to operationally engage the removable drive shaft cartridge to the prime mover, said shank is first fully engaged with said prime mover, wherein, in such position, the annular resilient element is engaged with the most forward of said first and second cam surfaces to generate a force on said prime mover carriage to urge said prime mover carriage in a direction which tends to longitudinally align the annular resilient element with the index groove.

* * * * *